United States Patent [19]

Roeper et al.

[11] Patent Number: 5,026,920
[45] Date of Patent: Jun. 25, 1991

[54] OBTAINING ALKANALS HAVING A 2-ALKYL BRANCH FROM ALKANAL MIXTURES

[75] Inventors: Michael Roeper, Wachenheim; Franz Merger; Joerg Liebe, both of Frankenthal; Armin V. Grenacher, Mutterstadt; Edgar Hahl, Ludwigshafen, all of Fed. Rep. of Germany

[73] Assignee: BASF Aktiengesellschaft, Ludwigshafen, Fed. Rep. of Germany

[21] Appl. No.: 433,661

[22] Filed: Nov. 8, 1989

[30] Foreign Application Priority Data

Dec. 15, 1988 [DE] Fed. Rep. of Germany ....... 3842186

[51] Int. Cl.$^5$ ...................... C07C 45/78; C07C 47/00
[52] U.S. Cl. .................... 568/492; 568/463; 568/464
[58] Field of Search ............... 568/463, 464, 492, 454

[56] References Cited

U.S. PATENT DOCUMENTS

| | | | |
|---|---|---|---|
| 4,247,485 | 1/1981 | Immel et al. | 568/464 |
| 4,258,214 | 3/1981 | Bahrmann et al. | 568/454 |
| 4,346,239 | 8/1982 | Bach et al. | 568/464 |
| 4,408,079 | 10/1983 | Merger et al. | 568/463 |

FOREIGN PATENT DOCUMENTS

| | | | |
|---|---|---|---|
| 1957301 | 3/1971 | Fed. Rep. of Germany | 568/464 |
| 1418367 | 4/1975 | United Kingdom | 568/463 |
| 2037769 | 7/1980 | United Kingdom | 568/464 |

OTHER PUBLICATIONS

J. Weber and P. Lappe, Methoden der Organischen Chemie (Houben-Weyl), Thieme, Stuttgart (1983), vol. E 3, p. 654.
F. J. Doering and G. V. Schaefer, J. Mol. Catal. 41 (1987), pp. 313–328.

*Primary Examiner*—Werren B. Lone
*Attorney, Agent, or Firm*—John H. Shurtleff

[57] ABSTRACT

Alkanals having a 2-alkyl branch are obtained from mixtures which contain the alkanals having a 2-alkyl branch in addition to n-alkanals, 3-alkylalkanals and/or further isomers by a process in which a) the alkanal mixture is reacted with an aqueous formaldehyde solution in the presence of a secondary amine and of a carboxylic acid as a catalyst, b) the aqueous phase containing the catalyst and any unconverted excess formaldehyde is separated off and c) the alkanals having a 2-alkyl branch are isolated by distillation from the condensates of the other alkanals with formaldehyde.

16 Claims, No Drawings

OBTAINING ALKANALS HAVING A 2-ALKYL BRANCH FROM ALKANAL MIXTURES

The present invention relates to a process for isolating alkanals having a 2-alkyl branch from mixtures which contain the alkanals having a 2-alkyl branch in addition to n-alkanals and alkanals having an alkyl branch in the 3-position or a higher position. The process is particularly suitable for separating the compounds 2-methylbutanal and 3-methylbutanal, which have the same boiling point.

In industrial syntheses of alkanals by hydroformylation of olefins, the alkanals are generally obtained not in pure form but as mixtures. Thus, 1-alkenes give alkanals having an additional carbon atom, n-alkanals, 2-methylalkanals and other alkanals being formed in different ratios depending on the catalyst system:

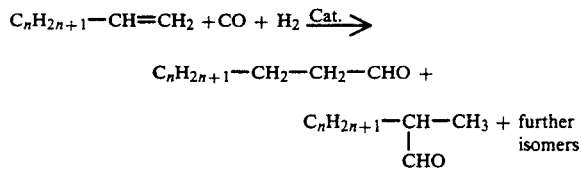

Although the n-alkanal is generally the desired product, there is also frequently interest in obtaining alkanals having a 2-alkyl branch and isolating them in high purity, since subsequent reactions may be sensitive to even traces of the isomeric alkanals.

However, the differences between the boiling points of the isomeric alkanals are so small that complete separation by distillation is impossible or uneconomical.

It is an object of the present invention to propose a process which permits the separation of isomeric alkanals having small differences between their boiling points.

A compilation of the processes known to date for the purification of aldehydes can be found in the summary by J. Weber and P. Lappe in Methoden der Organischen Chemie (Houben-Weyl), Georg Thieme Verlag Stuttgart, 1983, Volume E 3, page 654.

Furthermore, DE 22 18 305 states that long-chain n-alkanals can be isolated in pure form from alkanal mixtures by trimerization in the presence of acids, isolation of the solid trimeric n-alkanals (1,3,5-trioxanes) by filtration and subsequent thermal cleavage over $P_2O_5$.

For obtaining 2-methyldodecanal and n-tridecanal, DE 28 33 538 proposes thermal treatment of the isomer mixture during the distillation. In this procedure, the straight-chain alkanals are supposed to be converted into sparingly volatile compounds by condensation and to remain in the bottom product of the distillation, while 2-methyldodecanal can be taken off at the top. It is not stated whether this process can also be applied to mixtures which contain alkanals which have an alkyl branch in the 3-position or higher position.

However, it is known that alkanals having a 2-alkyl branch react significantly more slowly in aldol condensation reactions than n-alkanals or alkanals branched in the 3-position or a higher position. However, the effect cannot be utilized for the selective isolation of the alkanals having a 2-alkyl branch since they undergo a cocondensation reaction in alkanal mixtures (F. J. Doering and G. V. Schaefer, J. Mol. Catal. 41 (1987), 313–328).

This is also evident from the Comparative Examples A and B presented here, in which it is desired to obtain 2-methylbutanal (bp. 92.5° C./760 mm) from a mixture with 3-methylbutanal (bp. 92°–93° C./760 mm) in a ratio of 92:8 by base-catalyzed condensation. However, it is found that either the undesirable 3-methylbutanal does not react completely (Comparative Example B) or the predominant amount of the desired product 2-methylbutanal is lost through condensation with 3-methylbutanal (Comparative Example A).

We have found that this object is achieved and that, surprisingly, alkanals having a 2-alkyl branch can be obtained in high purity from mixtures which contain the alkanals having a 2-alkyl branch in addition to 2-alkanals, 3-alkylalkanals and further isomers if a) the alkanal mixture is reacted with an aqueous formaldehyde solution in the presence of a secondary amine and of a carboxylic acid as catalyst, b) the aqueous phase containing the catalyst and any unconverted excess formaldehyde is separated off and c) the alkanals having a 2-alkyl branch are obtained by distillation from the condensates of the other alkanals with formaldehyde.

The new method of purification is applied in particular to the mixture of valeraldehyde with its isomers, from which mixture 2-methylbutanal is obtained after the valeraldehyde has been separated off beforehand.

The known conditions of a Mannich condensation are suitable for the reaction with formaldehyde. Particularly suitable conditions are those of the process of DE 3 106 557, which is hereby incorporated by reference. According to this, the amounts of aqueous formaldehyde used are preferably such that a stoichiometric amount or excess of formaldehyde, calculated as 100% and based on the sum of the α-unsubstituted aldehydes in the mixture, is present and from 0.05 to 1.5 equivalents of carboxylic acid, i.e. mono- and dicarboxylic acids, and from 0.5 to 1 mole of amine, based in each case on one mole of formaldehyde used (calculated as 100%), are employed and the reaction with formaldehyde is carried out at a pH of from 2.5 to 7.

The 2-unsubstituted alkanals of the mixture can, however, generally be reacted with formaldehyde in less than the stoichiometric amount or in excess, preferably in about a molar amount or in excess, i.e. in an amount of from 0.9 to 10, preferably from 0.95 to 5, in particular from 1.0 to 2, moles of formaldehyde per mole of 2-unsubstituted alkanals.

The formaldehyde is expediently used in aqueous, advantageously from 20 to 60% strength by weight, solution. The acids used are aliphatic mono-, di- and polycarboxylic acids of 2 to 10 carbon atoms. The dicarboxylic acids and polycarboxylic acids (preferably including tricarboxylic acids) may also be aromatic and araliphatic carboxylic acids. Dicarboxylic acids and polycarboxylic acids are more advantageous than monocarboxylic acids. Examples of suitable substances are acetic acid, propionic acid, methoxyacetic acid, butyric acids, pentanoic, hexanoic, heptanoic, octanoic, nonanoic and decanoic acids, pivalic acid, 2-ethylbutyric acid, 2-methylpentanoic acid, 2-ethylhexanoic acid, isononanoic acid, pimelic acid, suberic acid, azelaic acid, sebacic acid, nonanedicarboxylic acid, decanedicarboxylic acid, butanetetracarboxylic acid, pentane-1,3,5-tricarboxylic acid, 3-hydroxyglutaric acid, saccharic acid, α,α'-dihydroxyadipic acid, preferably oxalic acid, succinic acid, glutaric acid, adipic acid, malic acid, tartaric acid, butane-1,2,4-tricarboxylic acid, 3-ethylpentane-1,3,5-tricarboxylic acid, citric acid, trimellitic acid, butanetetracarboxylic acid, pyromellitic acid, phthalic acid, terephthalic acid, isophthalic acid and fumaric acid, particularly preferably oxalic acid.

Advantageous amines are those of the formula

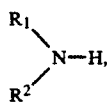

where $R^1$ and $R^2$ may be identical or different and are each alkyl of 1 to 12, advantageously 1 to 10, preferably 1 to 6, carbon atoms which is advantageously substituted by one or more heteroatoms, preferably by hydroxyl and/or secondary or tertiary amine, and $R^2$ and $R^3$ together with the adjacent carbon atom may furthermore form members of a ring which advantageously has 5 or 6 members and may also contain a nitrogen or oxygen atom. $R^2$ may furthermore be a radical

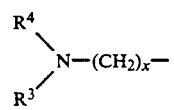

where $R^3$ and $R^4$ may be identical or different and are each alkyl of 2 to 18, advantageously 2 to 10, preferably 2 to 6, carbon atoms which is substituted by a plurality of hydroxyl groups, advantageously two hydroxyl groups, preferably one hydroxyl group, and $R^3$ may furthermore be an H atom and x is from 2 to 6. In monohydroxyalkyl radicals, the hydroxyl group is advantageously in the $\omega$-position. Secondary amines having a boiling point above 130° C. are preferred. Secondary amines having very low volatility, such as hydroxyalkylamines which can readily be obtained, for example, from ammonia or primary amines with alkylene oxides or amines having two or more amino groups, one or more of which are secondary and the others are secondary and/or tertiary, are particularly preferred.

Suitable specific secondary amines are: N-methyl-, N-ethyl-, N-propyl-, N-isopropyl-, N-butyl-, N-isobutyl-, N-sec-butyl-, N-tert-butyl-, N-pentyl-, N-hexyl-, N-heptyl-, N-octyl-, N-nonyl- and N-decylhydroxyethylamine; corresponding amines disubstituted by identical or different substituents from among those mentioned above; piperidine, morpholine, pyrrolidine, piperazine and N-methylpiperazine; N-ethyl-, N-propyl-, N-isopropyl-, N-butyl-, N-isobutyl-, N-sec-butyl-, N-tert-butyl-, N-pentyl-, N-hexyl-, N-heptyl, N-octyl-, N-nonyl- and N-decyl-N-hydroxyethylamine; corresponding amines substituted by an abovementioned hydroxyl-free substituent or by the hydroxypropyl and hydroxybutyl group; amines disubstituted by identical or different hydroxyalkyl substituents from among those mentioned above; N,N,N'-triethanolethylenediamine, N,N'-diethanolethylenediamine and homologous di- and tripropanol compounds and corresponding propylene- and butylenediamine compounds. Methylhydroxyethylamine, ethylhydroxyethylamine, isopropylhydroxyethylamine, butylhydroxyethylamine, isobutylhydroxyethylamine, methylhydroxypropylamine, ethylhydroxypropylamine, propylhydroxypropylamine, isopropylhydroxypropylamine, butylhydroxypropylamine, isobutylhydroxypropylamine, dihydroxyethylamine, dihydroxypropylamine, N,N,-diethanolethylenediamine, piperazine, N-methylpiperazine and dibutylamine are preferred.

In the case of monocarboxylic acids, advantageously from 0.05 to 1.5, expediently from 0.06 to 1.4, preferably from 0.03 to 1.25, in particular from 0.6 to 1.1, equivalents of monocarboxylic acid and advantageously from 0.05 to 1.5, preferably from 0.3 to 1.5, in particular from 0.6 to 1.2, equivalents of amine are used per mole of formaldehyde. In the case of di- or polycarboxylic acids, advantageously from 0.01 to 1.5, preferably from 0.05 to 1.5, in particular from 0.3 to 1.25, equivalents of di- or polycarboxylic acid and advantageously from 0.01 to 1.5, preferably from 0.05 to 1.5, in particular from 0.3 to 1.25, equivalents of amines are used per mole of formaldehyde. The ratio of carboxylic acid to amine is from 1 to 2, preferably from 1.05 to 1.8, in particular from 1.1 to 1.5, equivalents of carboxylic acid per equivalent of amine.

The reaction is carried out at a pH of from 2.5 to 7, preferably from 3 to 6.5, in particular from 3 to 6, at from 0° to 150° C., advantageously from 20° to 130° C., preferably from 30° to 120° C., particularly from 40° to 110° C. and under atmospheric pressure, superatmospheric pressure or reduced pressure, continuously or batchwise.

The reaction can be carried out as follows: the alkanal mixture, together with the amine, formaldehyde, water and acid, is kept at the reaction temperature for 1–300, as a rule 5–120, preferably 10–90, minutes. Thereafter, the 2-alkylalkanal is obtained from the reaction mixture by phase separation and distillation of the organic phase.

As shown for the Example of the methylbutanal mixture, 3-methylbutanal can be converted with formaldehyde selectively and completely into isopropylacrolein under the conditions according to the invention from a 92:8 mixture of 2- and 3-methylbutanal, while the 2-methylbutanal remains unchanged, in accordance with the following reaction:

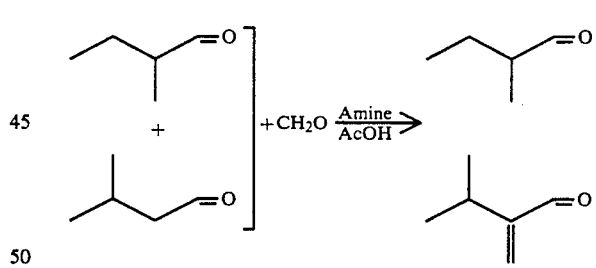

After the end of the reaction, the aqueous phase, which contains unconverted formaldehyde and the catalyst (carboxylic acid and secondary amine), is separated off. It can be reused, after the formaldehyde has been replenished.

2-Methylbutanal can then be isolated from the organic phase by distillation, without difficulties and in high purity, as a rule in a purity of more than 99%, since the difference in the boiling point compared with isopropylacrolein (bp. 108.5° C./760 mm) is 16° C. The isopropylacrolein remaining in the bottom product can likewise be used, if necessary after distillation.

The process can be applied to 2-alkylalkanals of not more than 20 carbon atoms, preferably $C_4$–$C_{13}$-alkanals, for separating these from the alkanals having the same number of carbon atoms, which is difficult to effect by distillation, particularly in the case of long-chain alkanals. For example, 2-methyldecanal (bp. 6°-364° C./0.5mbar) can be obtained from a mixture of n-undecanal (bp. 64°-66° C./0.5 mbar) as produced in the hydroformylation of 1-decene. The 2-methyldecanal is separated off by distillation without problems since the 2-nonylacrolein selectively formed from the n-undecanal has a substantially higher boiling point (bp. 80°-82° C./0.5 mbar). The 2-nonylacrolein remaining in the bottom product can likewise be used, if necessary after distillation.

The Examples show that, regardless of the chain length of the alkanal or of the alkyl radical in the 2-position, isolation of the alkanals having a 2-alkyl branch is substantially facilitated or becomes possible at all as a result of the novel process.

EXAMPLES

Example A (Comparative Example)

Experiment for the removal of 3-methylbutanal from 2-methylbutanal by condensation using methanolic KOH 10 ml of a 15% strength methanolic solution of KOH was slowly added dropwise to 100 g of an aldehyde mixture consisting of 92.2% of 2-methylbutanal, 7.3% of 3-methylbutanal and 0.2% of n-pentanal in a flask equipped with a magnetic stirrer, a dropping funnel, a reflux condenser and an internal thermometer. The internal temperature rapidly increased from room temperature to 55° C. and was kept at 50°-55° C. by means of an ice bath. After all of the potassium hydroxide solution had been added dropwise, stirring was continued for one hour at 50° C., after which the mixture was washed with 200 ml of water and analyzed by gas chromatography. The product contained 0.1% of 3-methylbutanal, 32.4% of 2-methylbutanal and 66.9% of high boiling condensates. The subsequent distillation over a 50 cm packed column under atmospheric pressure gave, as the main fraction at 92.5° C., 26.1 g of 2-methylbutanal having a purity of 99.5% and containing 0.4% of 3-methylbutanal.

Accordingly, the undesirable products 3-methylbutanal and n-pentanal could be substantially removed from the mixture but at the same time about 60% of the desired product 2-methylbutanal were converted into a condensate and thus lost.

Example B (Comparative Example)

Experiment for the removal of 3-methylbutanal from 2-methylbutanal by condensation using a reduced amount of methanolic KOH 2.4 ml of a 15% strength solution of KOH in methanol are added dropwise to 100 g of an aldehyde mixture of the same composition as in Comparative Example A in the same apparatus. The temperature was kept at 50°-55° C. by cooling with an ice bath. After all of the KOH solution had been added, stirring was continued for one hour at 50° C., after which the mixture was cooled to room temperature, neutralized with glacial acetic acid and washed with water. Gas chromatographic analysis gave a content of 1.1% of 3-methylbutanal, 64.4% of 2-methylbutanal, 0.01% of n-pentanal and 33.4% of high boiling condensates.

Although as much as about 28% of the desired product 2-methylbutanal were converted into high boiling condensates and thus lost, the reaction of the 3-methylbutanal was incomplete. The product was therefore not distilled.

Accordingly, because of the too low selectivity of the reaction, it is not possible by base-catalyzed aldol condensation to isolate alkanals having a 2-alkyl branch in high yield and hence economically.

EXAMPLE 1

Obtaining 2-Methylbutanal from a Pentanal Mixture 100 g of an aldehyde mixture consisting of 91.5% by weight of 2-methylbutanal, 7.8% by weight of 3-methylbutanal and 0.2% by weight of n-pentanal (3-methylbutanal + n-pentanal: 0.10 mole) were added to a mixture of 15 g of methylethanolamine (0.2 mole), 12 g of acetic acid (0.2 mole) and 20 g of 30% strength formaldehyde solution (0.2 mole) at 50° C. The mixture was stirred for one hour at 50° C., after which a sample of the organic phase was analyzed by gas chromatography; 89.6% by weight of 2-methylbutanal, 10.5% of isopropylacrolein (condensate of 3-methylbutanal and formaldehyde) and 0.2% by weight of a further product, presumably propylacrolein (condensate of n-pentanal and formaldehyde) were found. The subsequent distillation over a 50 cm packed column (wire gauze rings) under atmospheric pressure gave, as the main fraction at 92.5° C., 83.7 g of 2-methylbutanal having a purity of 99.6% by weight.

EXAMPLE 2

Obtaining 2-Methyldecanal from Undecanal Mixtures 243 g of an aldehyde mixture consisting of 70% by weight of n-undecanal (1 mole) and 30% by weight of 2-methyldecanal were added to a mixture of 112.5 g of 40% strength aqueous dimethylamine solution (1 mole), 60 g of acetic acid (1 mole) and 110 g of 30% strength by weight formaldehyde solution (1.1 mole) at from 55° to 60° C. After the mixture had been stirred for 3 hours at this temperature, gas chromatographic analysis of the organic phase showed that the n-undecanal had been completely converted into 2-nonylacrolein, while the 2-methyldecanal was present in unchanged form. The composition was 71.5% by weight of 2-nonylacrolein and 28.5% by weight of 2-methyldecanal. The subsequent distillation over a 60 cm packed column (wire gauze rings) under 0.5 mbar gave, as a first fraction at from 63° to 64° C., 62 g of 2-methyldecanal having a purity of 99.3%. 2-Nonylacrolein remained in the bottom product.

EXAMPLE 3

Obtaining 2-Methylhexanal from Heptanal Mixtures 386 g of a mixture of 41% by weight of 2-methylhexanal and 59% by weight of n-heptanal (bp. 42°-45° C./10 mbar) were added, with thorough stirring, to a solution of 75 g of methylethanolamine (1 mole) and 60 g of acetic acid (1 mole) in 210 g of 30% strength by weight formaldehyde solution (2.1 moles) at from 50° to 60° C. After 4 hours at 60° C., the organic phase was analyzed by gas chromatography and contained 38.5% by weight of 2-methylhexanal and 61% by weight of 2-pentylacrolein. The subsequent distillation over a 60 cm packed column gave 139 g of 2-methylhexanal (bp. 39°-40° C./10 mbar) having a purity of 99.2% by weight.

We claim:

1. A process for obtaining alkanals having a 2-alkyl branch from mixtures which contain alkanals having a 2-alkyl branch in addition to n-alkanals and 3-alkyl-alkanals and further isomers, such alkanals and further isomers having not more than 20 carbon atoms, which process comprises:

a) reacting the alkanal mixture with an aqueous formaldehyde solution in the presence of a secondary amine and a carboxylic acid as a catalyst, at a pH of from 2.5 to 7 and at a temperature of from 0° to 150° C.;

b) separating off the aqueous phase containing the catalyst and any uncovered excess formaldehyde; and c) isolating the alkanals having a 2-alkyl branch by distillation from the condensates of the other alkanals with formaldehyde.

2. A process as claimed in claim 1, wherein formaldehyde is used in about a molar amount or in excess, based on the sum of the 2-unsubstituted alkanals.

3. A process as claimed in claim 2, wherein from 0.05 to 1.5 equivalents of carboxylic acid and from 0.05 to 1.5 moles of amine, based on one mole of formaldehyde used (calculated at 100%), are employed.

4. A process as claimed in claim 1, wherein 2-methylbutanal is obtained from the mixture of the isomeric methylbutanals with valeraldehyde.

5. A process as claimed in claim 1 wherein step a) is carried out at a temperature of from 20° to 130° C.

6. A process as claimed in claim 1 wherein step a) is carried out at a temperature of from 30° to 120° C.

7. A process as claimed in claim 1 wherein step a) is carried out at a temperature of from 40° to 110° C.

8. A process as claimed in claim 1 wherein step a) is carried out at a pH of from 3 to 6.5.

9. A process as claimed in claim 1 wherein step a) is carried out at a pH of from 3 to 6.

10. A process as claimed in claim 1 wherein the catalyst is a monocarboxylic acid used in an amount of from 0.05 to 1.5 equivalents and an amine used in an amount of from 0.05 to 1.5 equivalents, in each case per mole of formaldehyde, and the ratio of equivalents of the monocarboxylic acid to the amine is from 1 to 2.

11. A process as claimed in claim 1 wherein the catalyst is a di- or poly-carboxylic acid used in an amount of from 0.01 to 1.5 equivalents and an amine used in an amount of from 0.01 to 1.5 equivalents, in each case per mole of formaldehyde, and the ratio of equivalents of the carboxylic acid to the amine is from 1 to 2.

12. A process as claimed in claim 1 wherein the formaldehyde is used as an aqueous solution having a strength of from 20 to 60%.

13. A process as claimed in claim 1 wherein the 2-alkylalkanals have from 4 to 13 carbon atoms.

14. A process as claimed in claim 1 wherein 2-methyldecanal is obtained from undecanal mixtures.

15. A process as claimed in claim 1 wherein 2-methylhexanal is obtained from heptanal mixtures.

16. A process as claimed in claim 1 wherein the carboxylic acid contains from 2 to 10 carbon atoms.

* * * * *